(12) United States Patent
Rutschmann et al.

(10) Patent No.: US 7,489,813 B2
(45) Date of Patent: Feb. 10, 2009

(54) METHOD AND SYSTEM FOR DETECTING THE THREE-DIMENSIONAL SHAPE OF AN OBJECT

(75) Inventors: Dirk Rutschmann, Stuttgart (DE); Marcus Josten, Stuttgart (DE)

(73) Assignee: corpus.e AG, Stuttgart (DE)

( * ) Notice: Subject to any disclaimer, the term of this patent is extended or adjusted under 35 U.S.C. 154(b) by 725 days.

(21) Appl. No.: 10/495,676

(22) PCT Filed: May 7, 2002

(86) PCT No.: PCT/EP02/05038

§ 371 (c)(1),
(2), (4) Date: Oct. 1, 2004

(87) PCT Pub. No.: WO03/044464

PCT Pub. Date: May 30, 2003

(65) Prior Publication Data

US 2005/0031193 A1    Feb. 10, 2005

(30) Foreign Application Priority Data

Nov. 21, 2001    (DE) ................. 101 56 908

(51) Int. Cl.
*G06K 9/00* (2006.01)
(52) U.S. Cl. .................... 382/154; 345/419; 702/127
(58) Field of Classification Search .............. 382/154
See application file for complete search history.

(56) References Cited

U.S. PATENT DOCUMENTS

| | | | | |
|---|---|---|---|---|
| 1,236,272 A | * | 8/1917 | Costley ................. | 177/5 |
| 4,535,782 A | | 8/1985 | Zoltan | |
| 4,969,106 A | * | 11/1990 | Vogel et al. ........... | 382/108 |
| 5,128,880 A | * | 7/1992 | White ................... | 382/165 |
| 5,457,325 A | * | 10/1995 | Huberty ............... | 250/559.29 |
| 5,911,126 A | * | 6/1999 | Massen ................ | 702/153 |

(Continued)

FOREIGN PATENT DOCUMENTS

DE    195 02 459 A1    8/1996

(Continued)

*Primary Examiner*—Matthew C. Bella
*Assistant Examiner*—Sath V. Perungavoor
(74) *Attorney, Agent, or Firm*—Stuart J. Friedman

(57) ABSTRACT

The invention relates to a method for detecting the three-dimensional shape of an object (2) during which an object (2) provided with photogrammetrically evaluable marks (4) is placed on a surface (5) at a predetermined location. This surface is provided with additional photogrammetrically evaluable marks (6) that are arranged in a predetermined manner with regard to one another. The surface extends in such a manner that the additional marks (6) are arranged around the contact surface of the object located on the surface. A number of images of the object (2) are taken from different views so that, in addition to the object (2), the surface (5) is also at least partially depicted. The three-dimensional shape of the object is determined from the images with the aid of the markers (4) of the object and of the markers (6) of the surface (5) by using a photogrammetric method. The inventive method enables slim objects to be digitized with a high degree of precision whereby eliminating the need for a scale that was placed in the images according to the prior art. The invention also relates to a system for implementing the method.

16 Claims, 2 Drawing Sheets

U.S. PATENT DOCUMENTS

Figure 1:
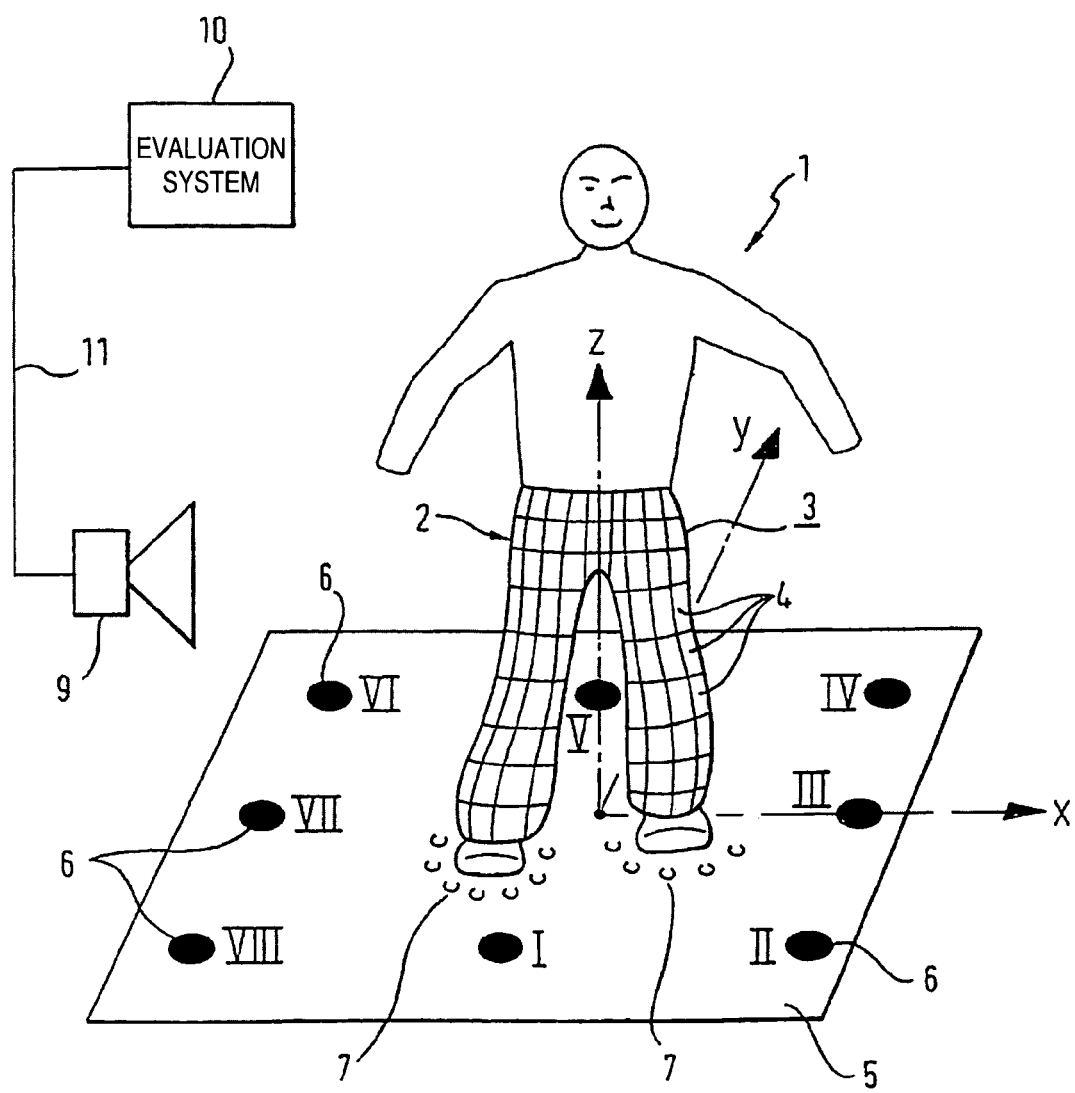

| | | | |
|---|---|---|---|
| 5,956,525 A * | 9/1999 | Minsky | 396/3 |
| 6,108,497 A | 8/2000 | Nakayama et al. | |
| 6,155,120 A | 12/2000 | Taylor | |
| 6,507,309 B2 * | 1/2003 | McMakin et al. | 342/22 |
| 6,546,356 B1 * | 4/2003 | Genest | 702/153 |
| 6,801,637 B2 * | 10/2004 | Voronka et al. | 382/103 |
| 7,095,886 B2 * | 8/2006 | Massen | 382/154 |
| 7,209,586 B2 * | 4/2007 | Massen | 382/154 |
| 7,298,889 B2 * | 11/2007 | Massen | 382/154 |
| 7,298,890 B2 * | 11/2007 | Massen | 382/154 |
| 7,433,502 B2 * | 10/2008 | Rutschmann | 382/128 |
| 2001/0024512 A1 * | 9/2001 | Yoronka et al. | 382/103 |
| 2002/0009222 A1 * | 1/2002 | McGibbon et al. | 382/154 |
| 2002/0191815 A1 * | 12/2002 | Meniere et al. | 382/103 |
| 2003/0012424 A1 * | 1/2003 | Franich et al. | 382/154 |
| 2003/0054327 A1 * | 3/2003 | Evensen | 434/252 |
| 2003/0137510 A1 | 7/2003 | Massen | |
| 2003/0215130 A1 * | 11/2003 | Nakamura et al. | 382/154 |
| 2004/0032595 A1 | 2/2004 | Massen | |
| 2005/0105772 A1 * | 5/2005 | Voronka et al. | 382/103 |

FOREIGN PATENT DOCUMENTS

| | | |
|---|---|---|
| DE | 196 34 254 A1 | 3/1997 |
| DE | 100 25 922 A1 | 12/2001 |
| DE | 100 49 926 A1 | 4/2002 |
| EP | 0 760 622 B1 | 11/1995 |
| EP | 0 958 782 A1 | 11/1999 |
| SU | 652 440 A | 3/1979 |
| WO | WO 94/20020 | 9/1994 |
| WO | WO 95/31934 | 11/1995 |

* cited by examiner

METHOD AND SYSTEM FOR DETECTING THE THREE-DIMENSIONAL SHAPE OF AN OBJECT

The invention relates to a method and to an arrangement for detecting the three-dimensional shape of an object, for example, a human leg.

Contact-free optical detection of the three-dimensional shape of bodies and parts of the body is very important when it comes to the automated customized manufacture of products that are to be fitted to an individual body shape such as, for example, orthopedic articles, custom-made shoes, form-fitting clothing, etc. Knowledge of the three-dimensional shape is also of special importance in the automated selection of fitting products from a catalog of prefabricated products. An example of this is the selection of fitting insoles from a large catalog of prefabricated insoles on the basis of the individual 3D data record of the shape of the customer's foot.

Numerous intricate scanning procedures are known for detecting three-dimensional shapes. EP 0 760 622 B1, for example, invented by Robert Massen, describes a particularly inexpensive method with which the body to be digitized is provided with an elastic, photogrammetrically marked covering and then photographed from a number of overlapping shooting positions. In this process, the part of the body does not have to be oriented in a very precise manner with respect to the camera and no calibrated shooting positions of the camera or cameras are needed, so that the requisite 2D images can even be taken free-handed with a digital camera.

German patent application DE 100 25 922.7 by the same inventor describes a number of suitable marking procedures that allow homologous pixels to be automatically found in the individual overlapping pictures and thus permit fully automated photogrammetric digitization.

German patent application DE 100 49 926.0 by the same inventor describes cameras which, by projecting reference marks, allow an ordered sequence of oriented shooting positions and thus a fully automatic acquisition of homologous pixels.

All of these methods based on photogrammetry work with marks attached to the body, which is especially disadvantageous when slim parts of the body marked by an elastic covering are to be taken, since then all of the marks are located essentially in a narrow section in the middle of the image of the taking camera. This applies to all overlapping three-dimensional positions that were taken from a panoramic view. Thus, the homologous pixels are likewise concentrated in a narrow section of every individual picture. This leads to large errors and uncertainties in the photogrammetric orientation of the individual pictures since the homologous image rays intersect each other at a flat angle and thus the intersection is not precisely defined in space. As a result, however, a precise determination of the three-dimensional shape of an object in the desired manner is not possible.

Moreover, with these prior art methods, a known straight segment has to be present in at least two pictures in order to obtain absolute space coordinates. Since the marks on the elastic covering do not define a specific straight segment in space, a known rigid scale has to be placed in the image field together with the body to be digitized. For purposes of photogrammetric evaluation, this scale has to be automatically recognized in the individual pictures and then evaluated separately from the photogrammetric marks of the body.

The objective of the invention is to create a method and an arrangement for the photogrammetric detection of the three-dimensional shape of an object, in which a more precise detection of the three-dimensional shape is possible, especially in the case of slim bodies. Moreover, according to the invention, the scale required with the prior-art methods has now become superfluous.

This objective is achieved by a method for detecting the three-dimensional shape of an object, in which an object provided with photogrammetrically evaluable marks is placed at a predetermined location on a surface that is provided with additional photogrammetrically evaluable marks arranged in a predetermined manner with respect to each other, wherein the surface extends in such a way that the additional marks are arranged around the contact surface of the object that is located on the surface, then a number of pictures of the object are taken from different views so that, in addition to the object, the surface is also at least partially depicted, and subsequently the three-dimensional shape of the object is determined from the taken pictures with the aid of the marks of the object and of the additional marks of the surface by using a photogrammetric method.

Moreover, this objective is achieved by an arrangement for detecting the three-dimensional shape of an object comprising photogrammetrically evaluable marks that have been applied onto the object, a shooting system and a system for evaluating the images and for determining the three-dimensional shape and moreover, said arrangement is characterized in that it has a surface that is provided with additional photogrammetrically evaluable marks arranged in a predetermined manner with respect to each other, wherein the surface extends in such a way that the additional marks are arranged around the contact surface of the object that is located on the surface.

Since the photogrammetric marks that define the arrangement on the surface can be configured in such a way that they are located in the image field of the individual shooting positions of a slim body that is to be digitized, far away from the detected marks of the body that are concentrated in the center of the field, they constitute homologous ray bundles that intersect at an obtuse angle, thus permitting a precise photogrammetric orientation of the individual shooting positions. In this manner, slim bodies can also be digitized with sufficient precision.

Moreover, the predetermined arrangement of marks on the surface can also replace the scale that has been commonly used so far since the defined distance between the photogrammetric marks of the mark arrangement applied onto the surface can serve as the scale.

Advantageous further developments of the invention are characterized in the dependent claims.

Figure 2:
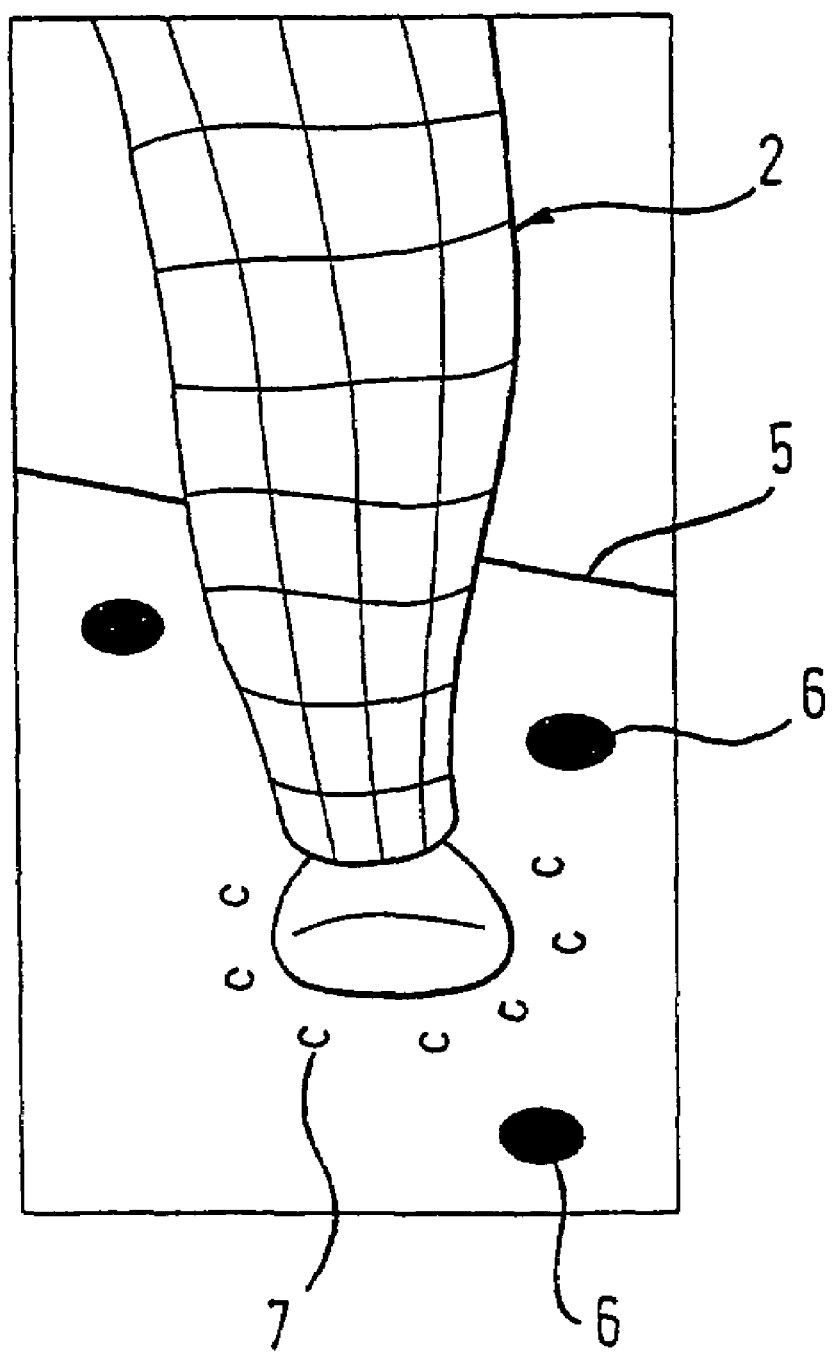

Additional features and advantages of the invention ensue from the following description of an embodiment on the basis of the drawings. The drawings show the following:

FIG. 1 a preferred embodiment of the invention with a plate-like coordinate system in which the object to be detected is the lower part of a human body;

FIG. 2 the image frame of a picture of the object to be detected that has been made according to the invention, as shown in FIG. 2;

The method according to the invention and the arrangement according to the invention will be described by way of an example with reference to the detection of the three-dimensional shape of the lower part of a human body for purposes of manufacturing compression stockings. However, the description of this example is not to be construed in a limiting fashion.

FIG. 1 shows the body 1 of a human. The three-dimensional shape of a part of the body 1, namely, the lower part 2 of the body, is to be detected. For this purpose, the lower part of the body is provided with an elastic covering in the form of pantyhose 3. Photogrammetric marks in the form of a grid have been applied onto the pantyhose 3, wherein the intersections of the grid lines define photogrammetrically evaluable dot marks 4.

The lower part 2 of the body stands on a plate 5 that forms a two-dimensional coordinate system (x-y axis). Photogrammetrically evaluable dot marks 6 that define the coordinate system have been applied onto the plate. The dot marks 6 have been applied at predetermined points on the plate 5 so that they define an x-y coordinate system. The dot marks 6 are arranged around the contact surface of the lower part of the body on the surface 5. In FIG. 1, this contact surface is defined by the soles of the shoes of the person wearing the pantyhose. The lower part 2 of the body is positioned on the plate in such a way that it has a certain orientation with respect to the x-y coordinate system. Here, additional markings 7 (not photogrammetrically evaluable) have been applied onto the plate and they are intended for the feet of the person so as to ensure a certain orientation of the lower part 2 of the body with respect to the surface. The known distance between any two dot-like plate marks 6 forms a straight segment in space and therefore constitutes a scale for obtaining absolute three-dimensional coordinates. The plane formed by the plate marks is, for example, the x-y plane of a world coordinate system on which the body of the patient is oriented approximately parallel to the z-axis. The zero point of this coordinate system is advantageously likewise established on the basis of the plate marks, for example, in the middle between two photogrammetric marks that lie opposite from each other.

First of all, several pictures of the lower part 2 of the body that is to be detected are taken from various views. The overlapping picture shooting positions are selected in such a way that at least in a few of the individual pictures, in addition to the marked section of the lower part 2 of the body, a section of the marked plate 5 can be likewise recognized. This is depicted in FIG. 2 which shows a section of a picture by way of an example. Here, the same reference numerals are used as in FIG. 1 for corresponding elements.

Since the plate marks 6 are located in the image field of the individual shooting positions far away from the marks of the leg that is to be digitized—said marks being concentrated in the center of the image field—they constitute ray bundles that intersect at an obtuse angle and thus they permit a precise photogrammetric orientation of the individual shooting positions. Therefore, according to the invention, all of the disadvantages described above regarding the known, very inexpensive methods are eliminated.

At the same time, the plate 5 defines a simple measuring space in which, for example, in an orthopedic retail shop, at the doctor's office, etc, the requisite panoramic pictures can be taken in the proper order. By using additional non-photogrammetric marks such as, for example, consecutively numbered reference marks associated with the individual shooting positions, the person operating the device can do the shooting in such a way that the individual overlapping pictures are taken in a predetermined sequence. In FIG. 1, this is indicated by Roman numerals.

Such reference marks are also useful to pre-orient the shooting camera 9 that is provided with a light mark projector. According to the invention, these non-photogrammetric marks are optically configured in terms of their coloring, texturing or shaping or by their reflection behavior in such a way that they can automatically be distinguished from the photogrammetric marks 4 and 6 by image processing methods.

The pictures taken in the manner described above are then evaluated with a known system 10 for evaluating the pictures and for determining the three-dimensional shape, and the three-dimensional shape of the object is determined on the basis of the homologous marks 4 and 6 that are on the object and that belong to the coordinate system. Here, for example, a computer can be used that has been programmed with appropriate software. If the shooting system 9 is a digital camera, then the digitized pictures can be transmitted in especially simple form via a connection line 11 or else wirelessly, to the evaluation system 10.

According to another embodiment of the invention, the marked plate 5 can also be equipped with additional measuring functions that are useful for the purpose in question. Thus, for example, the plate 5 can contain weighing scales in order to determine the weight of the patient concurrently with his/her three-dimensional shape. The plate can also contain a foot pressure sensor in order to measure the pressure distribution of the soles of the feet or to measure uneven pressure distribution on both feet as a result of body asymmetry.

The plate 5 can also contain sensors in order to determine the temperature distribution, the moisture distribution etc. of the soles of the feet.

According to another embodiment of the invention, the plate 5 can also contain actuators in order to effectuate certain positions of the body part that is to be digitized. Thus, for example, by using a motor-driven lever to position the foot, it can be brought into an anatomically desired position such as, for example, standing on tiptoe before the digitalization.

According to the invention, the rigid surface 5 can also be curved. Thus, for instance, in order to digitize a horizontal upper part of the body, it is useful to employ a cylindrical photogrammetrically marked contact surface that defines a cylindrical world coordinate system.

Another inventive idea is to make the surface of the plate 5 with a material that deforms under the load of the part of the body so that, on the basis of the photogrammetrically three-dimensional deformation of the surface measured in addition to the three-dimensional shape of the part of the body, it is possible to acquire information about physical properties of the body to be digitized. Thus, for example, from the deformation of the rigid plate, the weight of the body can be ascertained without the need for weighing scales. The deformation results from the shifting of the dot marks 6 that have been applied onto the plate. This shifting can be determined within the scope of the photogrammetric evaluation of the pictures.

For the person skilled in the art, it is obvious that the embodiment described above can, of course, be modified in such a way that the two-dimensional coordinate system on the surface (5) can be replaced by any desired predetermined arrangement of photogrammetrically evaluable marks. The only thing that is important is that this arrangement has to extend in such a manner that the additional marks 6 of the arrangement are positioned around the contact surface of the object located on the surface.

The invention claimed is:

1. A method for simultaneously detecting the absolute three-dimensional shape and physical properties of an object, comprising the steps of:

placing an object provided with photogrammetrically evaluable marks at a predetermined location on a surface thus defining a contact surface between said surface and said object, said surface being provided with additional photogrammetrically evaluable marks, said additional photogrammetrically evaluable marks being arranged in a predetermined manner with respect to each other in a way to define a coordinate system and a scale for obtaining absolute three-dimensional coordinates and being arranged around said contact surface, said surface being formed by a plate that contains at least one sensor which detects physical properties of said object, taking a number of overlapping pictures of said object from different views so that, in addition to said object, said surface is also at least partially depicted, and determining the three-dimensional shape of said object from said pictures with the aid of said marks of said object and of said additional marks of said surface by using a photogrammetric method, the photogrammetric method comprising acquisition of homologous pixels in overlapping pictures and determining the three-dimensional shape by calculating the intersection of homologous image rays.

2. The method according to claim 1, wherein said object is a human body or a part of a human body.

3. The method according to claim 1, wherein said object is provided with a covering onto which said photogrammetrically evaluable marks have been applied.

4. A method for simultaneously detecting the absolute three-dimensional shape and physical properties of an object, comprising the steps of:

placing an object provided with photogrammetrically evaluable marks at a predetermined location on a surface thus defining a contact surface between said surface and said object, said surface being provided with additional photogrammetrically evaluable marks, said additional photogrammetrically evaluable marks being arranged in a predetermined manner with respect to each other in a way to define a coordinate system and a scale for obtaining absolute three-dimensional coordinates and being arranged around said contact surface, said surface being formed by a plate that contains at least one sensor which detects physical properties of said object, said at least one sensor detecting at least one of the following quantities:

pressure distribution over the contact surface of the object placed on the surface;

temperature distribution;

moisture distribution of said object, taking a number of overlapping pictures of said object from different views so that, in addition to said object, said surface is also at least partially depicted, and determining the three-dimensional shape of said object from said pictures with the aid of said marks of said object and of said additional marks of said surface by using a photogrammetric method, the photogrammetric method comprising acquisition of homologous pixels in overlapping pictures and determining the three-dimensional shape by calculating the intersection of homologous image rays.

5. A method for simultaneously detecting the absolute three-dimensional shape and physical properties of an object, comprising the steps of:

placing an object provided with photogrammetrically evaluable marks at a predetermined location on a surface thus defining a contact surface between said surface and said object, said surface being provided with additional photogrammetrically evaluable marks, said additional photogrammetrically evaluable marks being arranged in a predetermined manner with respect to each other in a way to define a coordinate system and a scale for obtaining absolute three-dimensional coordinates and being arranged around said contact surface, said surface being formed by a plate that contains at least one sensor which detects physical properties of said object, wherein said surface deforms when said object is placed onto said surface and said deformation is measured by means of said at least one sensor by detecting the shifting of the additional photogrammetrically evaluable marks and determined with the aid of a photogrammetric method, and the weight of said object is computed on this basis, taking a number of overlapping pictures of said object from different views so that, in addition to said object, said surface is also at least partially depicted, and determining the three-dimensional shape of said object from said pictures with the aid of said marks of said object and of said additional marks of said surface by using a photogrammetric method, the photogrammetric method comprising acquisition of homologous pixels in overlapping pictures and determining the three-dimensional shape by calculating the intersection of homologous image rays.

6. A method for detecting the three-dimensional shape of an object, comprising the steps of:

placing the object provided with photogrammetrically evaluable marks at a predetermined location on a surface, said surface being provided with additional photogrammetrically evaluable marks which are arranged in a predetermined manner with respect to each other and which are arranged around said surface, said surface containing at least one sensor which detects physical properties of the object, taking a number of overlapping pictures of said object from different views so that, in addition to said object, said surface is also at least partially depicted, wherein the object is of a form that the photogrammetrically evaluable marks on the object are concentrated in a part of the image field and wherein said arrangement of said additional photogrammetrically evaluable marks on the surface and the individual shooting positions are chosen in such a way that said additional photogrammetrically evaluable marks are located in the image fields of the individual shooting positions far away from the marks on the object, and determining the three-dimensional shape of said object from said pictures with the aid of said marks of said object and of said additional marks of said surface by using a photogrammetric method, the photogrammetric method comprising acquisition of homologous pixels in overlapping pictures and determining the three-dimensional shape by calculating the intersection of homologous image rays.

7. The method according to claim 6, wherein said additional photogrammetrically evaluable marks on the surface are arranged in a way that they constitute ray bundles that intersect at obtuse angles at said individual shooting positions.

8. The method according to claim 6, wherein the additional photogrammetrically evaluable marks of said surface form a two-dimensional coordinate system and an absolute scale.

9. The method according to claim 8, wherein the coordinate system is defined by black dot marks that have been applied onto said surface at certain intervals from each other.

10. The method according to claim 6, wherein markings have been applied onto said surface which facilitate the orientation of said object on said surface.

11. An apparatus for detecting the three-dimensional shape of an object and simultaneously physical properties of the object, said arrangement comprising:

photogrammetrically evaluable marks that have been applied onto said object, a surface that is provided with additional photogrammetrically evaluable marks arranged in a predetermined manner with respect to each other in a way to define a coordinate system and a scale for obtaining absolute three-dimensional coordinates, said surface being formed on a plate that contains at least one sensor for detecting physical properties of said object, said object being located on said surface thus defining a contact surface between said object and said surface, said additional photogrammetrically evaluable marks being arranged around said contact surface, a shooting system for taking overlapping pictures of said object from different views so that, in addition to said object, said surface is also at least partially depicted, and a system for evaluating said pictures and for determining said three-dimensional shape of said object with the aid of said marks of said object and of said marks of said surface by using a photogrammetric method, the method comprising acquisition of homologous pixels in overlapping pictures and determining the three-dimensional shape by calculating the intersection of homologous image rays.

12. The apparatus according to claim 11, wherein markings have been applied onto said surface which facilitate the orientation of said object on said surface.

13. The apparatus according to claim 11, wherein said object is a human body or a part of a human body.

14. The apparatus according to claim 11, wherein said object is provided with a covering onto which said photogrammetrically evaluable marks have been applied.

15. An apparatus for detecting the three-dimensional shape of an object and simultaneously physical properties of the object, said arrangement comprising:

photogrammetrically evaluable marks that have been applied onto said object, a surface that is provided with additional photogrammetrically evaluable marks arranged in a predetermined manner with respect to each other in a way to define a coordinate system and a scale for obtaining absolute three-dimensional coordinates, said surface being formed on a plate that contains at least one sensor for detecting physical properties of said object, said at least one sensor detecting at least one of the following quantities:
a. pressure distribution;
b. temperature distribution,
c. moisture distribution
of said object said object being located on said surface thus defining a contact surface between said object and said surface, said additional photogrammetrically evaluable marks being arranged around said contact surface, a shooting system for taking overlapping pictures of said object from different views so that, in addition to said object, said surface is also at least partially depicted, and a system for evaluating said pictures and for determining said three-dimensional shape of said object with the aid of said marks of said object and of said marks of said surface by using a photogrammetric method, the method comprising acquisition of homologous pixels in overlapping pictures and determining the three-dimensional shape by calculating the intersection of homologous image rays.

16. An apparatus for detecting the three-dimensional shape of an object and simultaneously physical properties of the object, said arrangement comprising:

photogrammetrically evaluable marks that have been applied onto said object, a surface that is provided with additional photogrammetrically evaluable marks arranged in a predetermined manner with respect to each other in a way to define a coordinate system and a scale for obtaining absolute three-dimensional coordinates, said surface being formed on a plate that contains at least one sensor for detecting physical properties of said object, wherein said surface deforms when said object is placed onto said surface and wherein the deformation of said surface is determined with the aid of said system for evaluating the pictures and for determining the three-dimensional shape by detecting the shifting of the additional photogrammetrically evaluable marks, and the weight of said object is computed on this basis, said object being located on said surface thus defining a contact surface between said object and said surface, said additional photogrammetrically evaluable marks being arranged around said contact surface, a shooting system for taking overlapping pictures of said object from different views so that, in addition to said object, said surface is also at least partially depicted, and a system for evaluating said pictures and for determining said three-dimensional shape of said object with the aid of said marks of said object and of said marks of said surface by using a photogrammetric method, the method comprising acquisition of homologous pixels in overlapping pictures and determining the three-dimensional shape by calculating the intersection of homologous image rays.

* * * * *